(12) United States Patent
Marchau et al.

(10) Patent No.: US 6,562,281 B1
(45) Date of Patent: May 13, 2003

(54) METHOD FOR MAKING STERILIZED PLASTIC CONTAINERS, AND INSTALLATION THEREFOR

(75) Inventors: Bernard Marchau, Le Havre Cedex (FR); Patrick Mie, Le Havre Cedex (FR); Christian Bonnel, Le Havre Cedex (FR); Francois Quetel, Le Havre Cedex (FR)

(73) Assignee: Sidel, Le Havre Cedex (FR)

( * ) Notice: Subject to any disclaimer, the term of this patent is extended or adjusted under 35 U.S.C. 154(b) by 0 days.

(21) Appl. No.: 09/462,944
(22) PCT Filed: Jul. 16, 1998
(86) PCT No.: PCT/FR98/01552
§ 371 (c)(1),
(2), (4) Date: Mar. 17, 2000
(87) PCT Pub. No.: WO99/03667
PCT Pub. Date: Jan. 28, 1999

(30) Foreign Application Priority Data

Jul. 18, 1997 (FR) .............................................. 97 09335

(51) Int. Cl.⁷ ............................................... B29C 49/08
(52) U.S. Cl. ....................... 264/532; 264/534; 264/535; 425/524; 425/526
(58) Field of Search ................................. 264/532, 524, 264/525, 535, 534; 425/524, 526

(56) References Cited

U.S. PATENT DOCUMENTS

| | | | |
|---|---|---|---|
| 3,911,640 A | 10/1975 | Rausing | |
| 4,880,581 A | 11/1989 | Dastoli et al. | |

FOREIGN PATENT DOCUMENTS

| | | |
|---|---|---|
| DE | 196 42 987 A | 4/1998 |
| EP | 0 411 769 A | 2/1991 |
| EP | 0 464 933 A | 1/1992 |
| JP | 03290226 A * | 12/1991 |
| JP | 04044902 A * | 2/1992 |
| WO | WO 96 18541 A | 6/1996 |

OTHER PUBLICATIONS

Patent Abstracts of Japan, vol. 97, No. 002, Feb. 28, 1997 and JP 08 282789A.

* cited by examiner

*Primary Examiner*—Suzanne E. McDowell
(74) *Attorney, Agent, or Firm*—Sughrue Mion, PLLC

(57) ABSTRACT

In a system for manufacturing containers by blow-molding or drawing/blow molding of previously heated preforms, sterile containers (110) are obtained by wetting (45) the preforms (3) using an appropriated heat-activated sterilizing product by activating the product by heating means (100) which also provide a suitable heating profile to the preforms to prepare them for blowing.

31 Claims, 4 Drawing Sheets

METHOD FOR MAKING STERILIZED PLASTIC CONTAINERS, AND INSTALLATION THEREFOR

The invention relates to a procedure for manufacturing sterile containers of plastic material and a system for using it.

It applies most particularly to the manufacturing of sterile containers using preforms which are heated to bring them to their molding temperature (i.e., to a temperature at which the plastic material is softened), then introduced into a finishing mold where the final container is obtained by blow molding or drawing/blow molding of the preform.

One especially advantageous application is in line systems or even in combined systems (also called monobloc) for the manufacturing, filling and sealing of the containers in which the sterile containers are bottled, then capped immediately after their manufacture.

A combined or monobloc system is described in the French patent 74.37155 in the name of Société des Machines pour la Transformation des Plastiques: in this type of system, the manufacturing, the filling and the sealing of the containers takes place in one enclosure bathed in a flow of sterile air.

The patent U.S. Pat. No. 3,809,768 describes a line system, i.e., a system in which each part, having a specific function, is distinct from the others, and a sterile environment is maintained in each of the parts and, naturally, at the time of transfer between two successive parts.

In order to obtain sterile containers, various solutions have been considered.

One solution consists in sterilizing or decontaminating the containers before their manufacture, for example, by filling them with or immersing them in an appropriate sterilizing solution. This idea presents the following disadvantages:

1) First of all, after filling or immersion, it is necessary to drain the containers, possibly rinse them with a rinsing solution, then to dry them since the final contents of the container could be denatured by the sterilizing solution (or decontaminating solution), or the rinsing solution if the latter is used.

Thus, this solution is hard to use with an in-line filling system because of the time that it requires to use it.

2) In addition, after draining the containers, it is necessary to recover the sterilizing or decontaminating solution, the same is true with the rinsing solution, and to recycle it (them). In fact, it is not possible to imagine throwing the solution(s) away after a single use because of the considerable consumption that this would involve. Thus, it is necessary to provide a recycling system for each solution used. This creates systems that are very complicated and costly.

In addition, from the psychological point of view, the user may question the quality of the recycling.

Another solution consists in sterilizing the preforms before introducing them into the machine for manufacturing containers. In order to do this, the preforms are filled with a sterilizing/decontaminating solution by soaking or filling and maintained in contact with the solution for a certain period of time; the preforms are then drained and the traces of the solution are removed before the preforms are introduced into the heating furnace in preparation for blow molding them.

This solution presents the following disadvantages:

1) On one hand, the contact time between the sterilizing solution and each preform must be long (typically more than one minute with hydrogen peroxide ($H2O2$) and again the quality of the sterilization is variable from one preform to another), which involves a sterilizing system of significant complication to maintain the elevated production rates that are classically found in the blow molding or drawing/blow molding system;

2) The sterilizing system must be connected to the heating system by a sterile tunnel;

3) The draining of the preforms after sterilizing/decontaminating implies, as in the case of containers, collection of the cleaning solution and recycling it in a connected device.

The goal of the invention is to remedy the inconveniences of the type mentioned above by proposing a process and a system that is compatible with the high production rates of blow molding and which would be of minimum complication, naturally while still being efficient.

According to the invention, a procedure for obtaining a sterile container starting from a preform of thermoplastic material which is heated then blow molded or alternatively drawn and blow molded, is characterized in that it consists of 1) applying a sterilizing product that is activated by heat to the said preform, and 2) heating the said preform to simultaneously activate the said fluid and increase the temperature of said preform in order to reach the molding temperature, and 3) blow molding, alternatively drawing and blow molding the preform, to obtain the final container.

Thus, in heating the preform for simultaneously activating the sterilizing product and increasing the temperature of the preform in order to reach its blow molding temperature, a single operation is used to carry out the sterilizing and the softening of the material that makes up the preform in order to have it ready for blow molding. Thus the entire cycle is shortened.

In this way, it is no longer necessary to provide a special system for sterilizing since a common system is used for heating for the purposes of activating a sterilizing product and for softening the preform. Providing the means to apply the product to the preforms is sufficient.

In addition, there is an energy savings.

The operational safety of the sterilization is complete since the containers are blow molded immediately after the preforms have been sterilized: since the preforms are sterilized while being heated and the temperature at which they are introduced into the molds, then blow molded, is such that new germs cannot develop.

With the procedures of the previous type, according to which the preforms are sterilized, dried and transferred to the furnace, there exists a risk of pollution of the preforms during the transfer, for example if the sterile tunnel has a defect. This type of risk is eliminated here.

In addition, with the procedure according to the invention, the activation of the product by heat results in keeping the elements in contact with the preforms sterile at least in the heating zone. Thus it is not necessary to provide a flow of sterile air in this zone.

According to another characteristic, the application of the sterilizing product is proceeded by a phase of suppressing static electricity in the preform.

Thus, the particles and germs are more easily treated as a result since they are detached from the wall of the preform.

According to another characteristic, the product is a fluid and its application is carried out by wetting the preform.

Surprisingly, it has in fact been confirmed that it is not necessary to introduce large quantities of the product for sterilizing the preforms and that a simple wetting is adequate.

In one type of embodiment, the wetting is carried out when the preform enters the system upstream of the heating means by spraying the necessary quantity of the fluid into the preform in such a way as to moisten at least its entire interior surface.

In another method of embodiment, the wetting is carried out by filling the preform and then draining it without drying it before it is brought into the heating means.

This other method of embodiment presents the advantage, in comparison to the procedure that is the state of the art mentioned at the beginning, of requiring a recycling system of lesser performance since it is essential that the decontamination take place at the time of heating. The product of the draining is thus only slightly contaminated.

According to another characteristic, the quantity of the product placed in the preform is such that not just the preform leaves the heating means in a sterile condition, but all of the product evaporates at the time of heating, which avoids disturbances in the molding phase of the final container. In fact, traces of the product could be detrimental in obtaining proper molding.

In one method of embodiment, the final blow molding is carried out using air that is sufficiently filtered in order not to reintroduce undesirable particles.

Thus, it is possible to use a classic blow molding system with appropriate filters.

In another embodiment, the final blow molding is carried out using sterile air.

Other characteristics and advantages of the present invention will be evident from reading the description that follows, illustrated by the attached Figures, on which:

Figure 6:
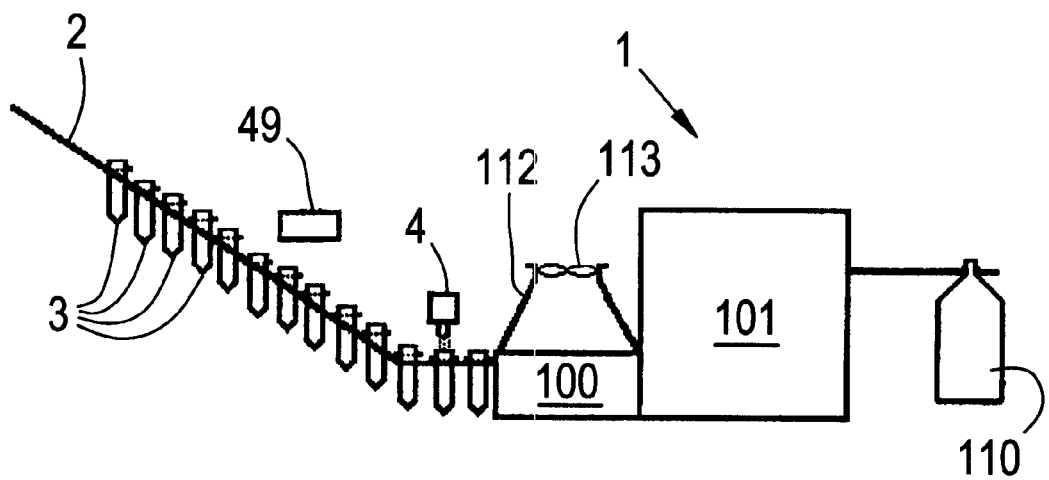
Figure 7:
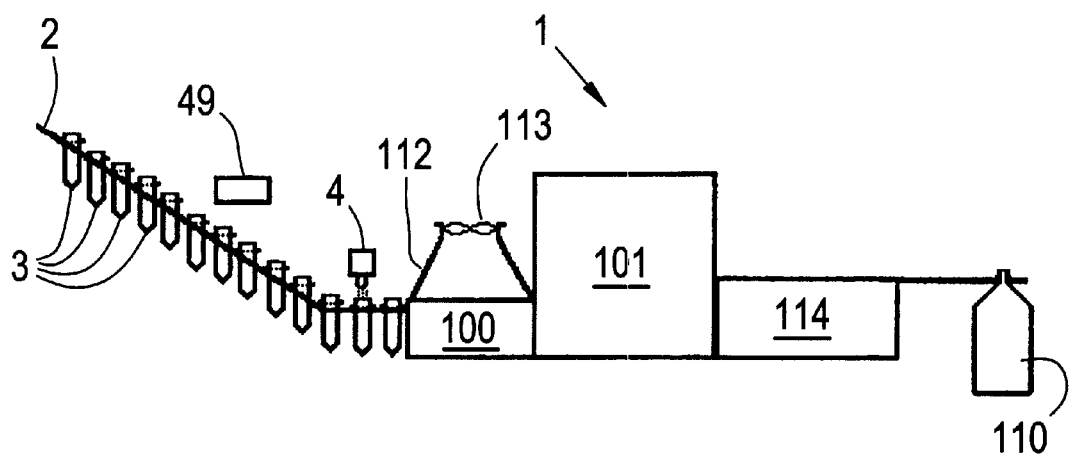
Figure 8:
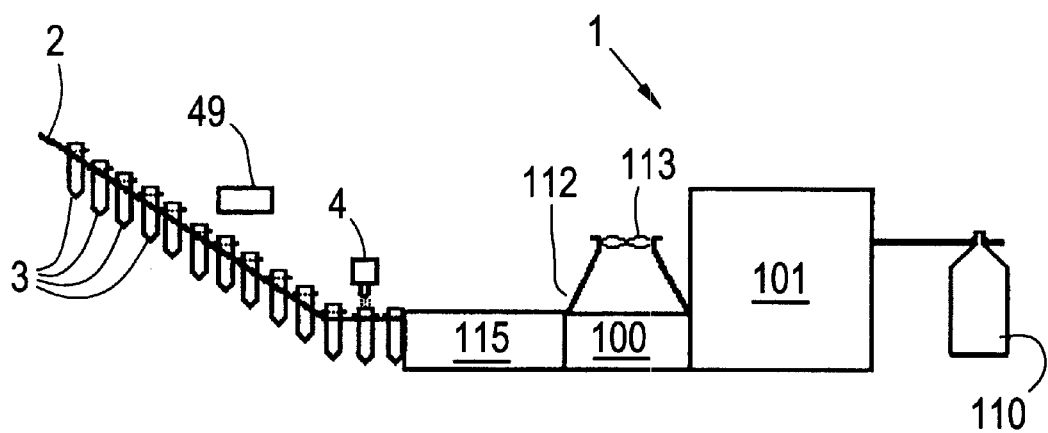

FIGS. 6 through 8 schematically illustrate improved variations.

Figure 1:
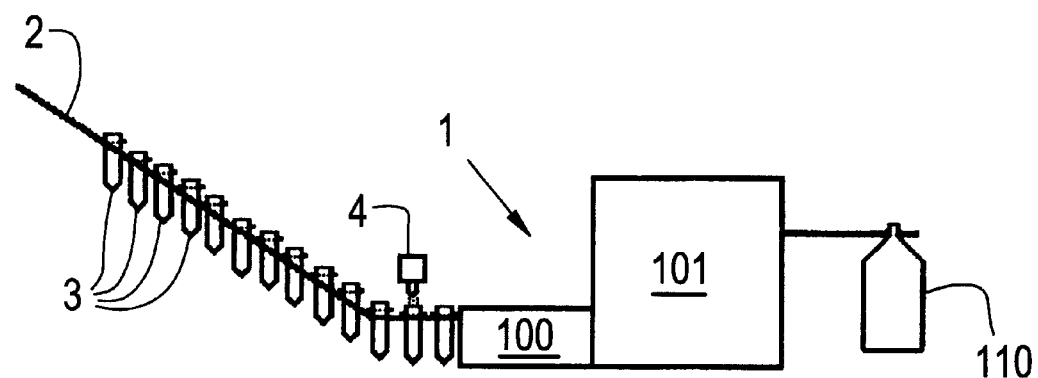
FIG. 1 is a schematic diagram of the invention.

FIG. 1 shows the schematic diagram of a system for using the procedure according to the invention.

The system, designated in general with reference number 1, is connected by a device 2 which brings the preforms 3 to a feed source for preforms 3 that is not shown. This source may consist in the known manner of a feed hopper and the device 2 is thus, for example, a feed rail. Alternatively, and without being limiting, the source may consist of an injection press for preforms with device 2 being a conveyor to bring the preforms.

System 1 comprises, in a known manner, the means 100 for heating, such as a furnace for bringing the preforms to their blow molding temperature (typically on the order of 100° C. to 150° C. when the material making up the preforms 3 is polyethylene terephthalate (PET). The preforms 3 brought by the carrying device 2 are introduced into the furnace 100 where they are thermally conditioned before being transferred into the device 101 for blow molding containers 110, such as a blow molding carousel or wheel.

In accordance with the invention, means 4 are provided upstream of the heating means 100 to apply the sterilizing product to at least the interior of the preforms 3.

Preferably, the sterilizing product is a chemical solution that can be activated by heat, typically an oxidizing solution such as a base solution of peracetic acid or, preferably, of hydrogen peroxide ($H_2O_2$) or any other appropriate solution.

In one implementation (FIG. 2), the means 4 are made up of a series of buses 41–44 running continuously and filling the preforms 3 in succession, for example, when they are located again at the carrying device 2. In this case, means are provided such as a vat 40 to recover the excess solution that comes from the preforms.

An embodiment of this type requires draining the preforms and returning them and recovering and recycling the drained product from the preforms and the vat 40. The draining of the preforms may be carried out in an advantageous manner at the beginning of the furnace in a zone 5, shown in FIG. 4, where the preforms are positioned neck down.

Nevertheless, this embodiment is not the most practical since it requires recovery of excess product at the time of filling and at the end of the draining as well as its recycling. However, it should be noted that, at the time of filling, the product is only very slightly polluted since it did not have the time to start to react, the activation taking place later by heating. Still, the degree of recycling is of lesser importance in comparison to that which is required with the procedure mentioned above of the prior type, with sterilizing the preforms upstream of the system.

Figure 5:
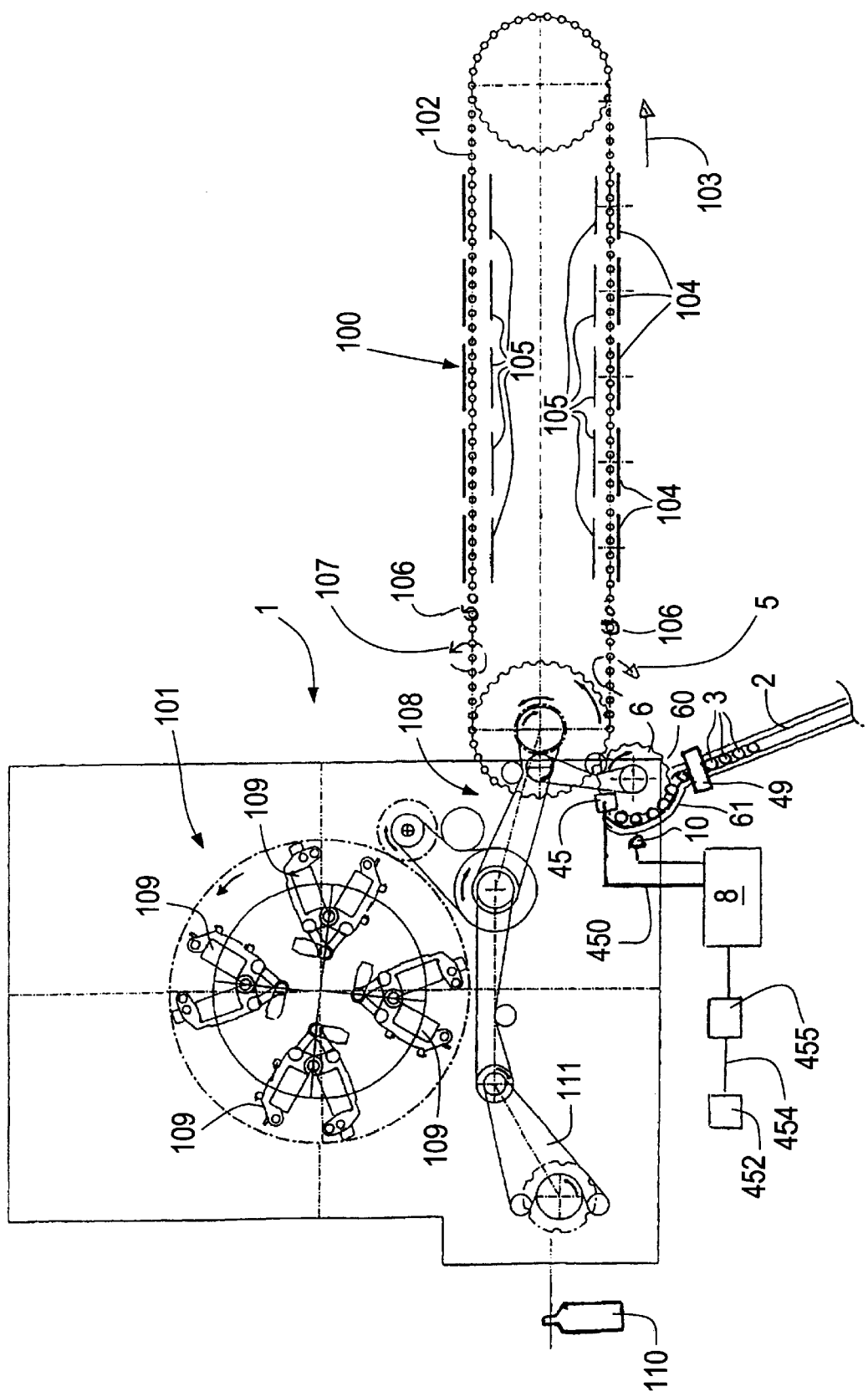
FIG. 5 is a more detailed diagram of a system to which the invention can be applied.

It is for this reason that, preferably (FIG. 3), means 4 are made up of an automatic sprayer 45 such as, for example, a sprayer with an electrical control placed either in front of device 2 for bringing the preforms, or a little further away between the device for bringing the preforms and the furnace 100, for example, in front of an intermediate element between the device 2 and the furnace 10, such as wheel 6 for loading the preforms that is used in the machines of the applicant and shown in FIG. 5.

The sprayer makes it possible to moisten the interior of the preforms with only the quantity necessary for sterilizing them, and the product then evaporates from the effect of the heat.

It has been confirmed, by way of an example, that spraying of 0.01 g to 0.07 g of hydrogen peroxide ($H_2O_2$) in the preforms intended for use for manufacturing 1-liter bottles make it possible to obtain excellent results.

This corresponds, for the standard preforms, to a necessary quantity that is less than one hundredth of the volume of the preforms, in fact it corresponds to volumes that are essentially between five hundredths and three thousandths of the total volume of the preforms.

Above one hundredth, traces of the product may exist at the output of the heating means 100, which involves a risk of interfering with the blow molding.

Figure 4:
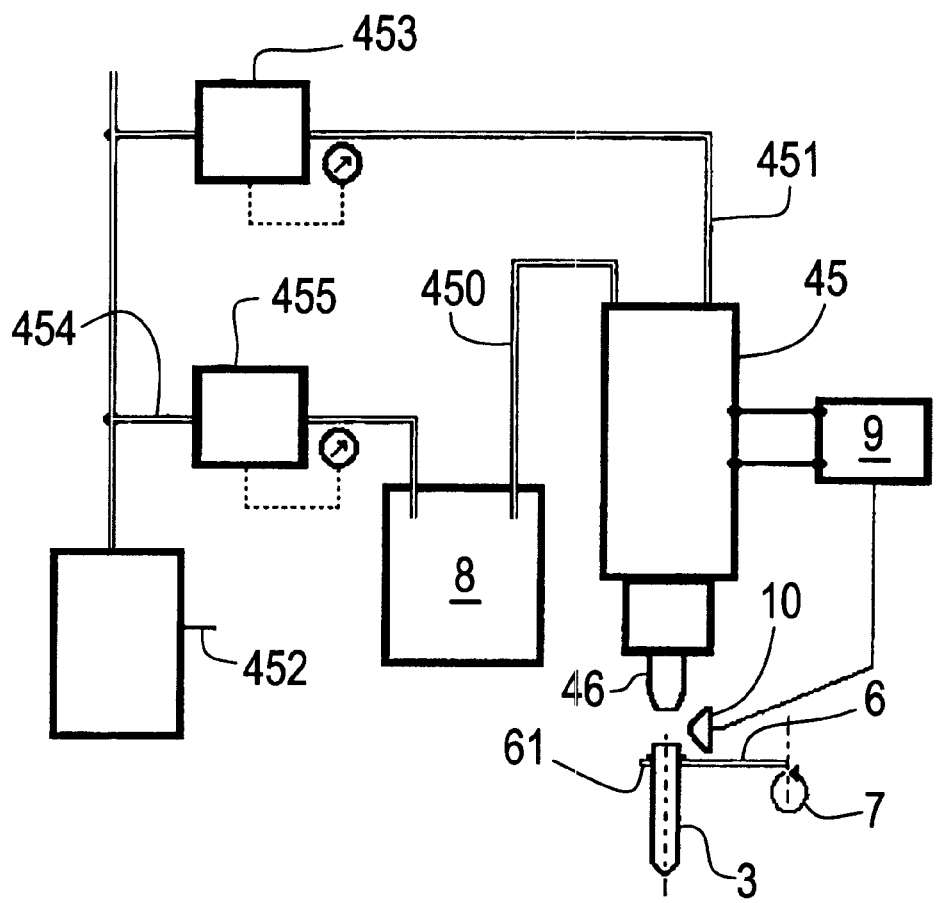

For this reason, on one hand, the sprayer is connected to a sensor, not shown in this Figure, but visible 10 in FIG. 4, to detect the arrival of each preform 3 and, on the other hand, is controlled in order to send the quantity of product necessary starting from the moment of detection.

Figure 3:
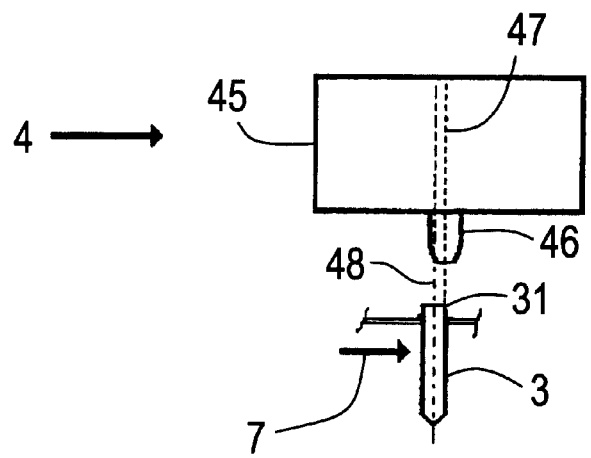
FIGS. 3 and 4 are schematic diagrams of one part of a second variation of the invention.

For example, supposing that the preforms move in the direction shown by arrow 7 in FIG. 3, the sprayer is controlled so that the spraying starts when the lip 31 of a preform 3 arrives across from the assembly 46 for spraying (dotted line 47 in FIG. 3) and stops when the assembly 46 is approximately across from the central axis 48 of the preform.

By acting thus, the entire interior wall and the base of the preforms are moistened enough to make an efficient sterilization possible when the product is activated by the heat in the furnace.

The consumption of the product gives evidence of the undeniable advantage that the invention presents: with hydrogen peroxide, of which the volumetric mass is close to that of water, around 30 grams of product is enough to treat 1,000 preforms intended to be 1 liter bottles. It would take 30 kilograms, thus 30 liters to treat 1,000 preforms and fill them all the way up, and 1,000 liters to treat 1,000 bottles by filling them all the way up.

In one embodiment, the sprayer 45 is made up of an automatic low-pressure gun, known in and of itself, in which the spraying is obtained by an assembly 46 made up of an air nozzle and a liquid nozzle. For example, the gun of the "Autojet" brand sold under reference number 28JJ AU by SPRAYING SYSTEMS Co. is used. It is equipped with a circular projection assembly 46 made up of a liquid nozzle and an air nozzle.

A gun of this type can be installed according to FIG. 4.

The gun 45 is connected to a sterilizing liquid reservoir 8 by way of a tube 450 which brings the reservoir into communication with the liquid nozzle, not referenced, of the spraying system 46.

A tube 451 for air supply places the air nozzle, not referenced, continuously in communication with an air supply source 452 (typically between 5 and 9 bars, but this range of values may vary).

A pressure-reducing valve 453 is connected between the low-pressure air source 452 and the tube 451 to regulate the pressure.

The reservoir 8 is subject to an internal pressure (typically between 0 and 7 bars). In the example shown in FIG. 4, the pressure is obtained by diverting 454 of air coming from the source 452 toward the pressure reducing valve 455 of which the output is connected to reservoir 8 in order to obtain the desired pressure in the latter.

A device 9 with electrical control connected to a sensor 10 for detecting the passage of preforms 3 sends orders to an electromagnetic circuit contained in the body of the gun to move the closing/opening needle of the liquid passage, itself contained in the body of the gun.

Preferably, as illustrated in FIG. 5, the means 49 are also provided for discharging the static electricity that the preforms contain. These means are upstream of the sprayer and are made up, in a preferred embodiment, of an ion generator which sends a flow of ionized air into the interior of the preforms. The air flow promotes the detachment of the particles and the ionization prevents the particles from adhering to the wall of the preforms.

As illustrated in FIG. 3, the supply of ionized air takes place, for example, when the preforms are on the carrying device 2 again (rail or conveyor), a little bit before the sprayer 45.

Figure 2:
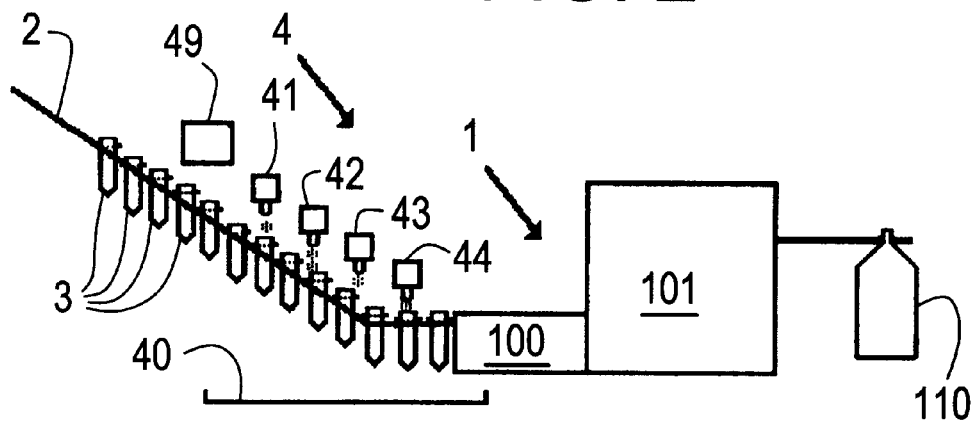
FIG. 2 is a schematic diagram illustrating a first embodiment of the invention.

A device 49 of this type has also been shown in FIG. 2. It may be used in any embodiment of the invention.

In addition, in FIG. 5 the manner in which the invention may be adapted to the known blow molding systems is illustrated such as the equipment manufactured by the applicant.

The preforms 3 are carried into the system by means such as a slide or rail 2. They are held on their neck between a wheel 6 with notches 60 and a semi-circular guide 61.

The sprayer 45 is placed above them in the path of the preforms 3, for example, in the zone where they are carried by the notches 60 of the wheel 6 and the guide 61, and the sensor 10 is then placed across from this zone to detect the arrival of a preform 3 below the sprayer.

In order to simplify this Figure, the pressure circuits for reservoir 8 and more generally the fluid circuits shown in FIG. 4 have not all been shown here.

After they have passed on the wheel 6, the preforms are held one by one by a chain 102, known in and of itself, transporting them into the furnace 100. The preforms 3, held by their necks, are carried in the direction illustrated by the arrow 103 and pass in front of the heating means (lamps 104 and reflectors 105). In addition, the preforms, after their introduction into the furnace, are returned to be placed neck down (arrow 5), then are rotated (arrow 106) at least during their passage in front of the heating means 104, 105.

At the furnace output, the preforms are placed neck up again (arrow 107) in order to be grasped by the transfer elements 108 to move them toward the finishing molds 109 of the blow molding carousel 101. The final containers 110 are then removed by appropriate means 111.

Thus it is understood that the invention is very easy to implement on the blow molding systems and does not require any modifications to them.

It is adequate to mount the sprayer 45 and its attached elements (reservoir 8, sensor 10) and to connect its air circuits to air circuits existing in the system.

However, it may be necessary to choose non-oxidizing materials which resist the sterilizing products, notably for the furnace 100 and the other elements that make up the system.

Other adaptations may be desirable which are illustrated in FIGS. 6 and 7.

On one hand, it may be preferable to provide an aspirating and evacuating assembly for residual vapors from the sterilizing product, for example, made up of a fume hood 112 and an aspirating turbine 113, arranged above the furnace 100 in FIGS. 6 and 7.

In the embodiment in FIG. 6, the blow molding assembly 101 uses sterile air to form the bottles. In addition to the sprayer 45, to its associated attached means, and the aspiration assembly 112, 113, it is preferable to provide an excess pressure using the sterile air in the system in order to avoid septic particles from penetrating into the interior.

The embodiment in FIG. 7, the blow molding assembly 101, uses not sterile air but filtered air and in this case an attached device 114 is provided at the output of this assembly 101 as a precaution to suppress or destroy any possible septic particles reintroduced at the time of blow molding. The attached device 114 is, for example, made up of a rinser using an appropriate decontamination product, and it may be completed by a drier for the containers 110, particularly to prevent the decontaminating product from changing the flavor of the bottled product.

Naturally, any other equivalent device that makes it possible to destroy contaminating particles that may be present in small quantities can be used.

In one variation, illustrated by FIG. 8 and applicable to the embodiment in FIG. 5 (on the condition that the configuration is slightly modified) and FIGS. 6 and 7, the preforms 3, after wetting by filling 41–44; then draining, or simple spraying 45, are introduced into a prior heating device 115 to accelerate the action of the sterilizing product and start raising their temperature in preparation for blow molding them.

Then they are transferred to the furnace 100, located downstream of device 115, in which they are subjected to an appropriate heating profile in preparation for blow molding and in which the decontamination continues and the product evaporation takes place because of the heat that is applied. The placement relative to the prior device 115 and the furnace 100 is such that the transfer between these two elements is carried out without significant heating of the preforms in order to avoid premature deactivation of the product and excessive energy consumption.

In fact, if the preforms had been cooled, there would have been no advantage in the energy plan and one of the advantages of the invention would then be lost.

A manufacturing system for sterile containers according to the invention may be directly connected to a bottling and/or capping system to make up either a monobloc system or an in-line system. In the latter case, it is necessary to provide a sterile tunnel between the output of the containers from the blow molder 100 and the entry into the bottler and/or the capper.

Naturally, the invention is not limited to the embodiments and the application that has been specifically illustrated: it is not restricted by them.

What is claimed is:

1. Procedure for obtaining a sterile container (110) from a preform (3) of thermoplastic material, comprising:
   1) applying (4, 41–44, 45) a heat-activated sterilizing product, to the said preform (3);
   2) heating the preform to simultaneously activate the said product and increase the temperature of the preform in preparation to reach its softening temperature; and
   3) molding (101) the said preform by blow molding, alternatively drawing and blow molding, to obtain the final container (110).

2. Procedure according to claim 1, characterized in that the application of the product is preceded by a phase for suppression of the static electricity present in the preform (3).

3. Procedure according to claim 2, characterized in that the suppression of static electricity present in the preform (3) is obtained by injection (49) of ionized air into the preform (3).

4. Procedure according to claim 2, characterized in that the product can evaporate and the volume of product applied is such that it is completely evaporated at the end of heating before molding.

5. Procedure according to claim 2, characterized in that the product is an oxidizing agent.

6. Procedure according to claim 5, characterized in that the product has a hydrogen peroxide base.

7. Procedure according to claim 5, characterized in that the product has a peracetic acid base.

8. Procedure according to claim 1, characterized in that the product is a liquid and that its application (4) to the preform is carried out by wetting at least the interior walls of said preform (3) with a volume of liquid adequate for sterilizing.

9. Procedure according to claim 8, characterized in that the wetting (4) is carried out by filling (41–44) then draining the preform without drying same so that a volume of liquid adequate for sterilizing remains.

10. Procedure according to claim 8, characterized in that the wetting (4) is carried out by spraying (45, 45) into the preform the volume of fluid adequate for sterilizing.

11. Procedure according to claim 8, characterized in that the volume of liquid is less than one hundredth of the total volume of the preform.

12. Procedure according to claim 11, characterized in that the volume of liquid is between five hundredths and three thousandths of the total volume of the preform.

13. Procedure according to claim 1, characterized in that the blow molding of a container (11) is carried out using a sterile fluid, such as sterile air, in such a way that the container can be filled and/or capped immediately after blow molding.

14. Procedure according to claim 1, characterized in that the blow molding of the container is carried out using filtered air and is completed, as a precaution, with an operation (114) for suppression and/or destruction of any septic particles that may be introduced at the time of blow molding in order to permit possible subsequent filling and/or capping.

15. Procedure according to claim 14, characterized in that the operation (114) consists of rinsing using an appropriate sterilizing product, such as a sterilizing liquid and a draining of the container.

16. Procedure according to claim 15, characterized in that the draining is followed by drying of the container.

17. Procedure according to claim 1, characterized in that the heating of the preform is carried out in two steps, a first one (115) to activate the product action and start increasing the temperature of the preform and a second one (100) to continue the action of the product, to evaporate it and to give the preform a specified heat profile in preparation for molding it.

18. System for implementation of the procedure according to claim 1, comprising the means (100, 115) for heating the preforms and the means for molding (101; 109) by blow molding, alternatively by drawing and blow molding of containers (110) from heated preforms (3), characterized in that it has, upstream of the heating means (100), means (4; 41; . . . 44; 45) for applying a heat-activated sterilizing product, to the said preforms (3) and the means to transfer the preforms with the product into the heating means in order to activate the product and bring the preforms to their softening temperature.

19. Procedure according to claim 18, characterized in that the sterilizing product is a liquid and in that the means for applying the product to the preform are arranged to wet the preforms.

20. Procedure according to claim 19, characterized in that the means for wetting the preforms are made up on one hand by a series of buses (41–44) located above the path of the preforms upstream of the system, in order to fill the preforms when they pass in line in front of these buses, and on the other hand by the means (5) to return and drain the preforms without drying them.

21. Procedure according to claim 20, characterized in that the means for returning the preforms are made up of returning means (5) to place the preforms neck down in the heating means (100).

22. Procedure according to claim 19, characterized in that the means for wetting the preforms are made up of a sprayer (45), such as an electrically-controlled low pressure automatic gun.

23. Procedure according to claim 22, characterized in that the gun is fed with air (451) and with spraying liquid (45) and the passage of the liquid is controlled by a control element (9) activated by a sensor (10) that senses the position of the preforms.

24. Procedure according to claim 18, characterized in that the heating means (100) to activate the product and bring the preforms to their molding temperature are made up of the furnace (100) for thermal conditioning of the preforms in preparation for molding them.

25. Procedure according to claim 18, characterized in that the heating means are made up, on one hand, by a heating enclosure (115) downstream of the means (4) for applying the sterilizing product and, on the other hand, by the furnace (100) for heating the preforms for their thermal conditioning in preparation for molding the final containers, the said furnace (100) is downstream of the enclosure (115) and transfer means are provided between the enclosure (115) and the furnace (100) and are arranged so that the preforms will not become cooled when they go from the enclosure to the furnace.

26. Procedure according to claim 18, characterized in that it has means for blowing the sterile air into the preforms in preparation for molding them into final containers (110).

27. Procedure according to claim 18, characterized in that it has means for blowing the filtered air into the preforms in preparation for molding them into final containers (110).

28. Procedure according to claim 27, characterized in that it has means (114) to carry out an operation of suppression and/or destruction of septic particles possibly reintroduced at the time of blow molding, such as an operation of rinsing and draining of the containers (110).

29. Procedure according to claim 18, characterized in that it has, upstream from the means (4; 41–44; 45) for applying the sterilizing product, means (49) to suppress the static electricity present in the preforms.

30. Procedure according to claim 29, characterized in that the means for suppressing static electricity comprise a device (49) for injecting ionized air into the preforms.

31. Procedure according to claim 18, characterized in that it is connected to a system for filling and/or capping the containers (110).

* * * * *